(12) United States Patent
Kawakami et al.

(10) Patent No.: US 11,767,327 B2
(45) Date of Patent: Sep. 26, 2023

(54) COMPOUND, PATTERN FORMING SUBSTRATE, COUPLING AGENT, AND PATTERN FORMATION METHOD

(71) Applicants: NIKON CORPORATION, Tokyo (JP); Kanagawa University, Yokohama (JP)

(72) Inventors: Yusuke Kawakami, Yokohama (JP); Kazuo Yamaguchi, Yokohama (JP)

(73) Assignees: NIKON CORPORATION, Tokyo (JP); KANAGAWA UNIVERSITY, Yokohama (JP)

(*) Notice: Subject to any disclaimer, the term of this patent is extended or adjusted under 35 U.S.C. 154(b) by 845 days.

(21) Appl. No.: 16/744,949

(22) Filed: Jan. 16, 2020

(65) Prior Publication Data
US 2020/0148700 A1 May 14, 2020

Related U.S. Application Data

(63) Continuation of application No. PCT/JP2018/026909, filed on Jul. 18, 2018.

(30) Foreign Application Priority Data

Jul. 19, 2017 (JP) .................................. 2017-140046

(51) Int. Cl.
C07D 495/04 (2006.01)
C07D 409/12 (2006.01)
(Continued)

(52) U.S. Cl.
CPC ......... C07D 495/04 (2013.01); C07D 409/12 (2013.01); C07F 7/0834 (2013.01);
(Continued)

(58) Field of Classification Search
CPC . C07D 195/04; C07F 7/0834; H01L 51/0074; H01L 51/0094
See application file for complete search history.

(56) References Cited

U.S. PATENT DOCUMENTS

2006/0222865 A1 10/2006 Hoshino et al.
2014/0206872 A1 7/2014 Isobe et al.
2014/0217374 A1 8/2014 Melucci et al.

FOREIGN PATENT DOCUMENTS

CN 102593363 A 7/2012
CN 104941681 A 9/2015
(Continued)

OTHER PUBLICATIONS

Japanese Office Action dated Jan. 5, 2021, in corresponding Japanese Patent Application No. 2017-140046.
(Continued)

Primary Examiner — Anthony Ho

(57) ABSTRACT

What is provided is a compound, a pattern forming substrate, a coupling agent, and a pattern formation method. The compound is represented by Formula (1).

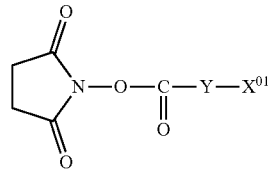

[in the formula, $X^{01}$ represents a group exhibiting semiconductor characteristics and Y represents a divalent linking group]

3 Claims, 1 Drawing Sheet

(51) Int. Cl.
  *C07F 7/08*   (2006.01)
  *G03F 7/075*  (2006.01)
  *H10K 71/00*  (2023.01)
  *H10K 85/40*  (2023.01)
  *H10K 85/60*  (2023.01)
(52) U.S. Cl.
  CPC .......... *G03F 7/075* (2013.01); *H10K 71/621* (2023.02); *H10K 85/40* (2023.02); *H10K 85/6576* (2023.02)

(56) References Cited

FOREIGN PATENT DOCUMENTS

| | | |
|---|---|---|
| CN | 105980600 A | 9/2016 |
| EP | 1 736 477 A1 | 12/2006 |
| EP | 2 710 012 B1 | 6/2015 |
| JP | 2002-275144 | 9/2002 |
| JP | 4997765 | 8/2012 |
| JP | 2012-177104 | 9/2012 |
| JP | 2012-207104 | 10/2012 |
| JP | 2014-522393 | 9/2014 |
| JP | 2017-120342 | 7/2017 |
| TW | 201404781 A | 2/2014 |
| WO | WO 2012/111142 A1 | 8/2012 |
| WO | WO 2012/156948 A1 | 11/2012 |
| WO | WO 2013/042012 A1 | 3/2013 |

OTHER PUBLICATIONS

Office Action, dated Apr. 28, 2022, in Chinese Patent Application No. 201880046689.8 (20 pp.).

Decision of Rejection, dated Dec. 15, 2022, in corresponding Chinese Patent Application No. 201880046689.8 (21 pp.).

Office Action dated Jul. 28, 2021 in Taiwanese Patent Application No. 107124738.

Jin Zhu et al., "A Surface Modification Approach to the Patterned Assembly of Single-Walled Carbon Nanomaterials", Nano Letters, 2003, vol. 3, No. 9, pp. 1239-1243.

Manuela Melucci et al., "Facile covalent functionalization of graphene oxide using microwaves: bottom-up development of functional graphitic materials", Journal of Materials Chemistry, 2010, vol. 20, No. 41, pp. 9052-9060.

Manuela Melucci et al., "Facile tuning from blue to white emission in silica nanoparticles doped with oligothiophene fluorophores", Journal of Materials Chemistry, 2010, vol. 20, No. 44, pp. 9903-9909.

Manuela Melucci et al., "Multicolor, large-area fluorescence sensing through oligothiophene-self-assembled monolayers", Chemical Communications (Cambridge, United Kingdom), 2011, vol. 47, No. 6, pp. 1689-1691.

Barbara Cosimelli et al., "A New Synthetic Route to 2,2':5',2"-Terthiophene-5-derivatives to Conjugate with Proteins and Monoclonal Antibodies", Tetrahedron, 1996, vol. 52, No. 34, pp. 11281-11290.

International Search Report dated Oct. 2, 2018 in corresponding International Patent Application No. PCT/JP2018/026909.

Written Opinion of the International Searching Authority dated Oct. 2, 2018 in corresponding International Patent Application No. PCT/JP2018/026909.

Mouffouk et al., "Electrosynthesis and characterization of biotin-functionalized poly(terthiophene) copolymers, and their response to avidin", J. Mater. Chem., 2005, vol. 15, pp. 1186-1196.

Bauerle, et al., "Post-Polymerization Functionalization of Conducting Polymers: Novel Poly(alkylthiophene)s Substituted with Easily Replaceable Activated Ester Group", Adv. Muter., 1995, vol. 8, No. 3, pp. 214-218.

Office Action, dated Nov. 2, 2021, in Chinese Patent Application No. 201880046689.8 (35 pp.).

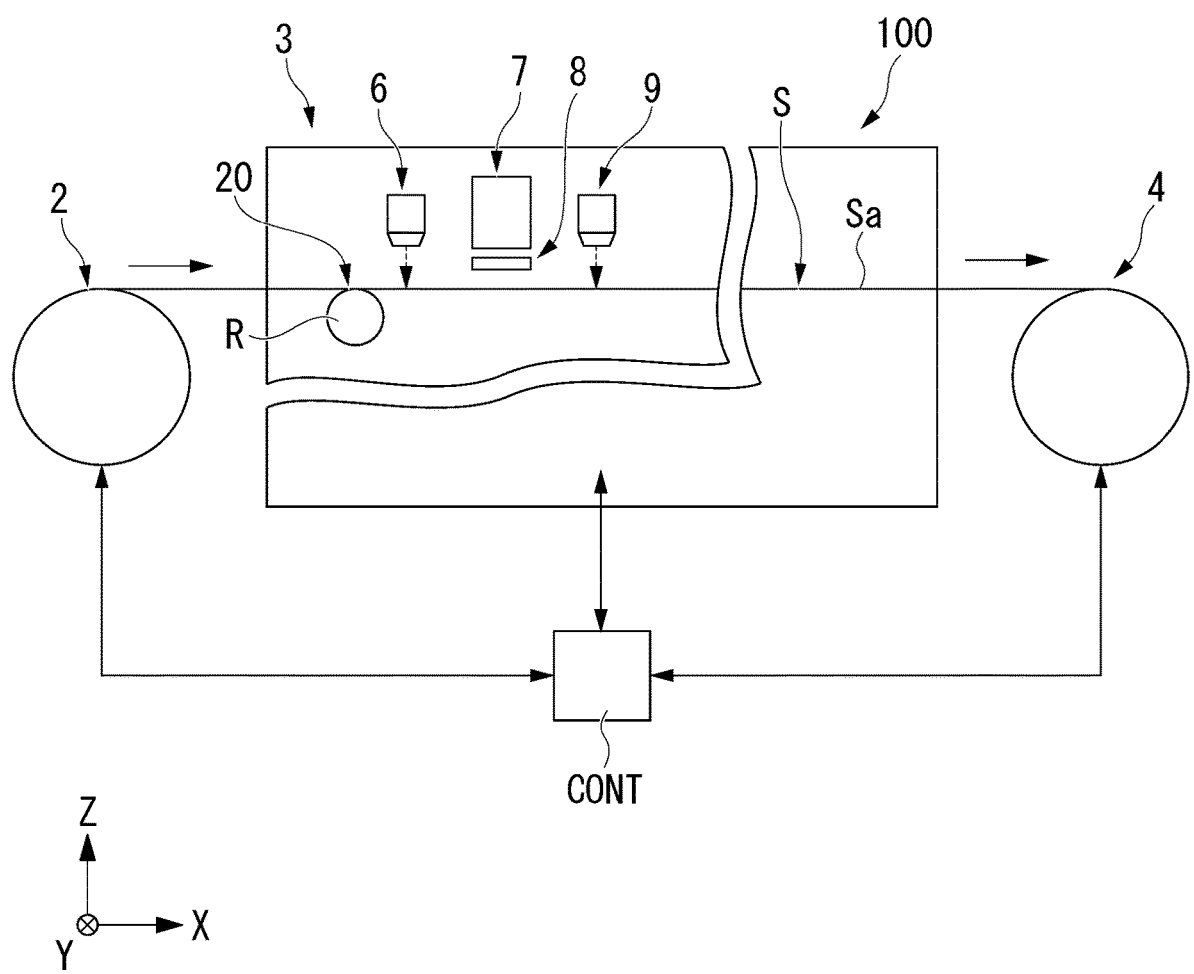

COMPOUND, PATTERN FORMING SUBSTRATE, COUPLING AGENT, AND PATTERN FORMATION METHOD

CROSS-REFERENCE TO RELATED APPLICATIONS

This application is a Continuation Application, under 35 U.S.C. § 111 (a), of International Patent Application No. PCT/JP2018/026909, filed on Jul. 18, 2018, which claims foreign priority benefit under 35 U.S.C. § 119 of Japanese Patent Application No. 2017-140046 filed on Jul. 19, 2017 in the Japanese Intellectual Property Office, the contents of both of which are incorporated herein by reference.

TECHNICAL FIELD

The present invention relates to a compound, a pattern forming substrate, a coupling agent, and a pattern formation method.

BACKGROUND ART

Recently, in production of fine devices such as semiconductor elements, integrated circuits, and devices for organic EL displays, a method of forming patterns having different surface characteristics on a substrate to prepare a fine device using their differences in surface characteristics has been suggested.

As a pattern formation method using the differences in surface characteristics on a substrate, a method of forming a hydrophilic region and a water-repellent region on a substrate and coating the hydrophilic region with an aqueous solution containing a functional material is exemplified. According to this method, since the aqueous solution containing a functional material spread and wets only in the hydrophilic region, a thin film pattern for the functional material can be formed.

As the material which is capable of forming a hydrophilic region and a water-repellent region on a substrate, for example, Patent Document 1 discloses a fluorine-containing compound which is capable of changing the contact angle before and after irradiation with light.

CITATION LIST

Patent Literature

[Patent Document 1] Japanese Patent No. 4997765

DISCLOSURE OF INVENTION

According to a first embodiment of the present invention, there is provided a compound represented by Formula (1).

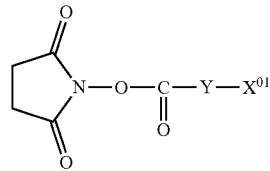

(1)

[in the formula. $X^{01}$ represents a group exhibiting semiconductor characteristics and Y represents a divalent linking group]

According to a second embodiment of the present invention, there is provided a pattern forming substrate, which has a surface chemically modified by the compound according to the first embodiment of the present invention.

According to a third embodiment of the present invention, there is provided a coupling agent which is formed of the compound according to the first embodiment of the present invention.

According to a fourth embodiment of the present invention, there is provided a pattern formation method of forming a pattern on a surface to be treated of a target object, including: a first step of aminating at least a part of the surface to be treated of the target object to form an aminated surface; and a second step of chemically modifying the aminated surface using the compound according to the first embodiment of the present invention.

According to a fifth embodiment of the present invention, there is provided a pattern formation method of forming a pattern on a surface to be treated of a target object, including: Step A of aminating at least a part of the surface to be treated of the target object using a first photodegradable coupling agent including a compound having a photoresponsive group; Step B of introducing a group having semiconductor characteristics onto the surface to be treated using a first coupling agent containing a compound including a group having semiconductor characteristics, after Step A; and Step C of introducing a group having semiconductor characteristics using a second coupling agent including the compound according to claim 1 or 2, after Step B.

According to a sixth embodiment of the present invention, there is provided a compound represented by Formula (B1).

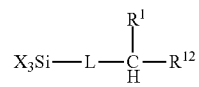

(B1)

[in Formula (B1), X represents a halogen atom or an alkoxy group, $R^1$ represents a hydrogen atom or a linear, branched, or cyclic alkyl group having 1 to 10 carbon atoms, $R^{12}$ represents a substituent having a thiophene skeleton, and L represents a divalent linking group including (—NH—) or a methylene group]

According to a seventh embodiment of the present invention, there is provided a compound represented by Formula (B1)-1.

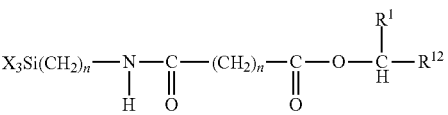

(B1)-1

[in Formula (B1)-1, X represents a halogen atom or an alkoxy group, $R^1$ represents a hydrogen atom or a linear, branched, or cyclic alkyl group having 1 to 10 carbon atoms, $R^{12}$ represents a substituent having a thiophene skeleton, and n represents an integer of 0 or greater]

BRIEF DESCRIPTION OF DRAWINGS

FIG. 1 is a schematic view showing the overall configuration of a substrate treatment device.

BEST MODE FOR CARRYING OUT THE INVENTION

<Compound>

A present embodiment of the present invention relates to a compound represented by Formula (1).

A compound of the present embodiment includes an active carbonate structure and a group having semiconductor characteristics. For this reason, the compound of the present embodiment can simultaneously perform modification of an aminated substrate and introduction of a semiconductor characteristic group. That is, it is possible to omit a step of forming a wiring formation base film by using a compound of the present invention and to form an organic semiconductor base film.

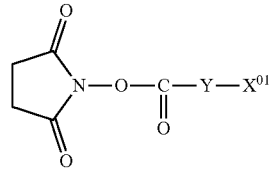

(1)

[in the formula. $X^{01}$ represents a group exhibiting semiconductor characteristics and Y represents a divalent linking group]

{$X^{01}$}

In Formula (1), $X^{01}$ represents a group exhibiting semiconductor characteristics.

The "semiconductor characteristics" in the present specification indicates that the conductive characteristics change due to external stimuli such as light and voltage, and particularly means that a drain-source current changes due to a gate voltage.

In the present embodiment, a group exhibiting semiconductor characteristics as $X^{01}$ is preferably a group obtained by removing one hydrogen atom from the compound exhibiting semiconductor characteristics. Examples of the compound exhibiting semiconductor characteristics include the following compounds.

As a p-type semiconductor, there are acenes such as pentacene, rubrene, and tetracene and thiophenes such as benzodithiophene (BDT)/benzothieno benzothiophene (BTBT)/dinaphthieno thiophene (DNTT)/dinaphthobenzodithiophene (DNBDT).

As an n-type semiconductor, there are perylenes such as perylene diimide (PTCDI), quinones such as tetracyanoquinodimethane (TCNQ), and fullerenes such as C60.

In a case where fullerenes are used as the n-type semiconductor, it is possible to introduce a molecule including an ester structure into fullerene by using thereof as a precursor.

As a compound having the semiconductor characteristics, a compound into which a soluble structure such as an alkyl group and an alkyl silyl group are introduced may be used. As such a compound, examples thereof include soluble pentacene such as TIPS pentacene (6, 13-Bis(triisopropylsilylethynyl) pentacene).

{Y}

In Formula (1), Y represents a divalent linking group. In the present embodiment, Y is not particularly limited, but a divalent hydrocarbon group which may have a substituent, a divalent linking group including a hetero atom, and the like are preferable exemplary examples.

Divalent hydrocarbon group which may have substituent

In a case of the divalent hydrocarbon group which may have a substituent, the hydrocarbon group is preferably an aliphatic hydrocarbon group. As the aliphatic hydrocarbon group, a linear or branched aliphatic hydrocarbon group, an aliphatic hydrocarbon group including a ring in the structure, and the like are exemplary examples.

Among these, a linear or branched aliphatic hydrocarbon group is preferable, a linear or branched alkylene group having 1 to 20 carbon atoms is preferable, a linear or branched alkylene group having 1 to 15 carbon atoms is more preferable, and a linear or branched alkylene group having 1 to 10 carbon atoms is still more preferable.

Divalent Linking Group Including Hetero Atom

In a case of a divalent linking group including a hetero atom, as the preferable linking group, a linking group containing —O—. —C(=O)—O—, —C(=O)—, —O—C(=O)—O—, —C(=O)—NH—. —NH—, —NH—C(=NH)—, —S—, —S(=O)$_2$—, and —S(=O)$_2$—O— is preferable.

As Y, a group in which an ester bond [—C(=O)—O—] and a linear or branched alkylene group is combined with each other is preferable.

In the present embodiment, it is preferable that Formula (1) is Formula (1)-1.

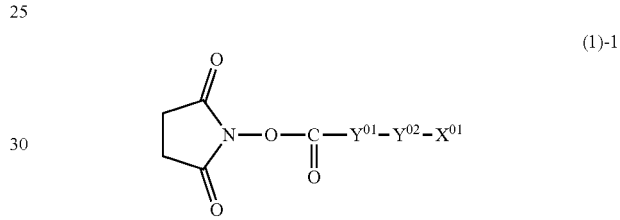

(1)-1

[in Formula (1)-1, $Y^{01}$ represents an alkylene group having 1 to 20 carbon atoms, $Y^{02}$ represents a linking group including —O—, —C(=O)—O—, —C(=O)—, —O—C(=O)—O—, —C(=O)—NH—, —NH—, —NH—C(=NH)—, —S—, —S(=O)$_2$—, or —S(=O)$_2$—O—, and $X^{01}$ represents a group exhibiting semiconductor characteristics]

In Formula (1)-1, as $Y^{01}$, the same group as the alkylene group exemplified in the Y is exemplified, but among these, a linear alkylene group is preferable, and an alkylene group having 4 to 15 carbon atoms is more preferable.

In the present embodiment, it is preferable that Formula (1)-1 is Formula (1)-1-1.

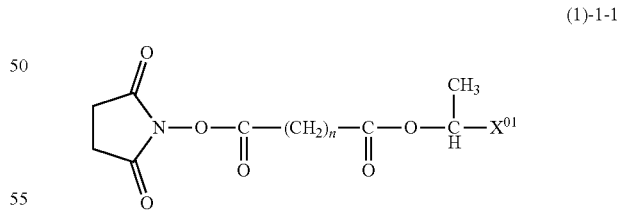

(1)-1-1

[in the formula, $X^{01}$ represents a group exhibiting semiconductor characteristics and n represents an integer of 1 to 20]

{n}

In Formula (1)-1-1, n represents an integer of 1 to 20, preferably 1 to 15, more preferably 5 to 10, and particularly preferably 7 or 10.

Hereinafter, specific examples of the compound represented by Formula (1) will be described below. In the following specific examples, n represents any one integer of 1 to 20, but 1 to 15 are preferable, 5 to 10 are more preferable, and 7 or 10 is particularly preferable.

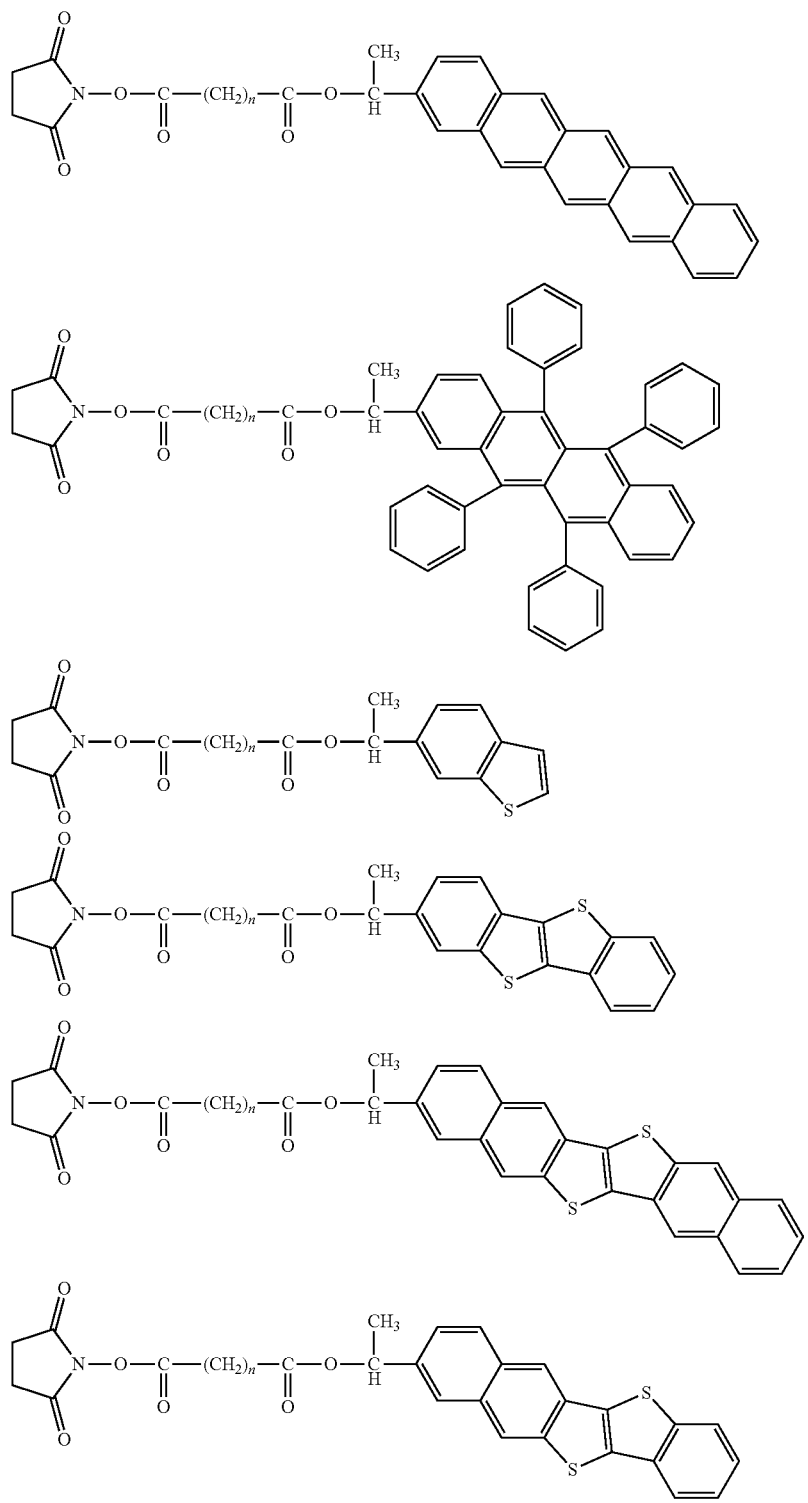

<<Method of Producing Compound>>

The compound represented by Formula (1) according to the present embodiment can be produced using the following method.

[Step 1]

First, an acetyl group is introduced into the compound exhibiting semiconductor characteristics. Subsequently, as shown in the following reaction formula, the acetyl group is deprotected to generate a hydroxyl group.

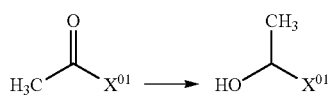

[in the formula, $X^{01}$ is a group obtained by removing one hydrogen atom from a compound exhibiting semiconductor characteristics]

[Step 2]

Subsequently, a compound represented by the formula (HOOC—Y') is reacted with the compound obtained in Step 1.

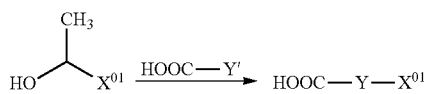

[in the formula, $X^{01}$ is a group obtained by removing one hydrogen atom from a compound exhibiting semiconductor characteristics, Y is a divalent linking group, and Y' is a group obtained by adding one hydrogen atom to Y]

[Step 3]

Subsequently, di(N-succinimidyl) carbonate is reacted with the compound obtained in Step 2 to obtain a compound of the present embodiment.

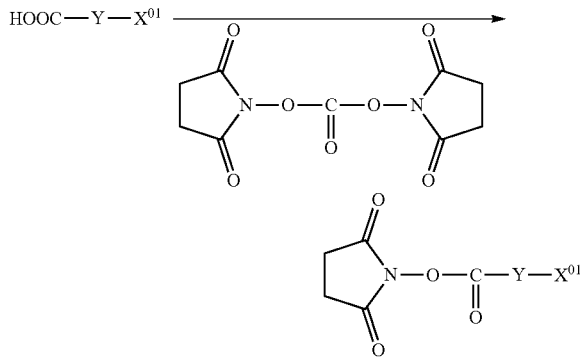

[in the formula. $X^{01}$ is a group obtained by removing one hydrogen atom from a compound exhibiting semiconductor characteristics and Y is a divalent linking group]

In Steps 1 to 3, examples of a solvent to be used include ethyl acetate, butyl acetate, acetone, methyl ethyl ketone, methyl isobutyl ketone, cyclohexanone, tetrahydrofuran, dioxane. N,N-dimethyl formaldehyde, N,N-dimethyl acetoamide, benzene, toluene, acetonitrile, methylene chloride, chloroform, dichloroethane, methanol, ethanol, 1-propanol, 2-propanol, and 1-butanol. These may be used alone or a combination of two or more thereof may be used.

<Pattern Forming Substrate>

A pattern forming substrate of a second embodiment of the present invention is chemically modified using a compound of the first embodiment of the present invention. That is, a functional group having semiconductor characteristics is introduced into a substrate. For this reason, it is possible to suitably dispose an organic semiconductor material dispersed or dissolved in a semiconductor material dispersion medium having a similar mother skeleton to that of the introduced semiconductor characteristic group.

The base material is not particularly limited, and preferred examples thereof include glass, quartz glass, a silicon wafer, a plastic plate, and a metal plate. Further, a substrate on which a metal thin film is formed may be used on these substrates.

The shape of the base material is not particularly limited, and a flat surface, a curved surface, or a flat surface which is partially curved is preferable, and a flat surface is more preferable. Further, the area of the base material is not particularly limited, and a base material having a surface with a size as large as a coating method of the related art can be applied can be employed. Further, it is preferable that the surface chemically modified using the compound according to the first embodiment is formed on one flat surface of the base material on the plane.

In a case where a surface of a substrate is modified, it is preferable that the surface of the substrate is subjected to a pre-treatment in advance. As the pre-treatment method, a pre-treatment carried out using a piranha solution or a pre-treatment using a UV-ozone cleaner is preferable.

<Coupling Agent>

A third embodiment of the present invention relates to a coupling agent formed of the compound according to the first embodiment.

According to the coupling agent of the present embodiment, since the coupling agent is formed of a compound including a group having semiconductor characteristics, it is possible to introduce a semiconductor characteristic group onto a surface to be treated of a target object.

<Pattern Formation Method 1>

According to a fourth embodiment of the present invention, there is provided a pattern formation method of forming a pattern on a surface to be treated of a target object, including: a first step of aminating at least a part of the surface to be treated of the target object to form an aminated surface; and a second step of chemically modifying the aminated surface using the compound according to the first embodiment of the present invention.

According to the present embodiment, it is possible to form a pattern in which a group having semiconductor characteristics is introduced into the surface to be treated of the target object.

[First Step]

First, at least a part of the surface to be treated of the target object is aminated to produce an aminated surface. In the present step, for example, a substrate containing an amino group is produced by acting 3-aminopropyltrimethoxysilane on a substrate containing a hydroxyl group as described below.

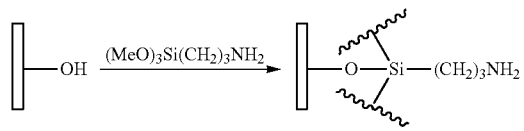

[Second Step]

A second step is a step of chemically modifying the aminated surface produced in the first step using the compound of the first embodiment of the present invention. The compound of the first embodiment of the present invention has an active carbonate structure and a group having semiconductor characteristics, and thus it is possible to perform simultaneously modification of an aminated substrate and introduction of a group having semiconductor characteristics.

The object is not particularly limited, and examples thereof include a metal, a crystalline material (such as a monocrystalline material, a polycrystalline material, and a partially crystalline material), an amorphous material, a conductor, a semiconductor, an insulator, an optical element, a coated substrate, fibers, glass, ceramics, zeolite, plastic, thermosetting and thermoplastic materials (such as polyacrylate, polycarbonate, polyurethane, polystyrene, a cellulose polymer, polyolefin, polyamide, polyamide, a resin, polyester, and polyphenylene which are occasionally doped), a film, a thin film, and foil.

In the pattern formation method according to the present embodiment, it is preferable that a circuit pattern for an electronic device is formed on a flexible substrate.

In the present embodiment, for example, a resin film or foil such as stainless steel can be used as the flexible substrate serving as an object. Examples of the resin film include materials such as a polyethylene resin, a polypropylene resin, a polyester resin, an ethylene vinyl copolymer resin, a polyvinyl chloride resin, a cellulose resin, a polyamide resin, a polyimide resin, a polycarbonate resin, a polystyrene resin, and a vinyl acetate resin.

Here, the flexibility indicates a property in which the substrate can be bent without being cut or fractured even in a case where a force with a degree of the own weight of the substrate is applied to the substrate. Further, the concept of the flexibility also includes a property in which the substrate is bent by a force with a degree of the own weight of the substrate. Further, the flexibility varies depending on the material of the substrate, the size, the thickness, or the environment such as the temperature. In addition, as a substrate, a single strip-shaped substrate may be used or a substrate having a configuration in which a plurality of unit substrates is connected to be formed into a strip shape may be used.

A method of chemically modifying the surface to be treated of the target object is not particularly limited as long as the carbonate group in Formula (1) is bonded to the substrate, and a known method such as an immersion method or a chemical treatment method can be used.

An example of chemical modification in the present step will be described.

The chemical modification in the present step can be performed by, for example, reacting the compound represented by Formula (1) with the substrate containing an amino group which has been produced in a pre-step as described below.

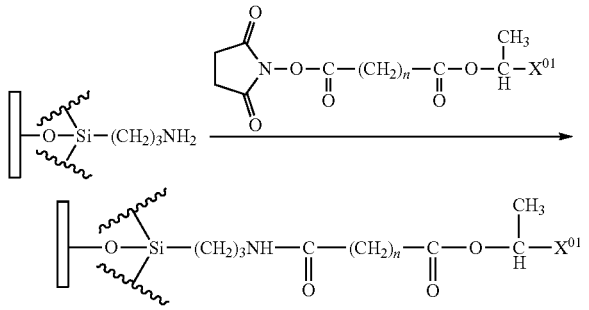

[in the formula, $X^{01}$ represents a group exhibiting semiconductor characteristics and n represents an integer of 1 to 20]

<Pattern Formation Method 2>

A fifth embodiment of the present invention is a pattern formation method of forming a pattern on the surface to be treated of the target object, including: Step A of aminating at least a part of the surface be treated using a first photodegradable coupling agent including a compound having a photo-responsive group; Step B of introducing a group having semiconductor characteristics onto the surface to be treated using a first coupling agent containing a compound including a group having semiconductor characteristics, after Step A; and step C of introducing a group having semiconductor characteristics using a second coupling agent including the compound of the first embodiment of the present invention, after Step B.

According to the pattern formation method 2, it is possible to introduce a group having semiconductor characteristics at a high density.

[Step A]

The present step is a step of aminating at least a part of the surface to be treated using the first photodegradable coupling agent including a compound having a photo-responsive group.

{Pre-Treatment Step}

Before Step A, it is preferable to perform pre-treatment on the surface to be treated of the target object, before modifying the surface to be treated of the target object. As the pre-treatment method, a pre-treatment carried out using a piranha solution or a pre-treatment using a UV-ozone cleaner is preferable. As the object, it is possible to use the same object as the object described in the pattern formation method of the fourth embodiment of the present invention.

The amination of Step A is not particularly limited as long as the first photodegradable coupling agent including a compound having a photo-responsive group is combined with a substrate, and it is possible to use a known method such as an immersion method and a chemical treatment method.

The compound having a photo-responsive group contained in the photodegradable silane coupling agent used in Step A is not particularly limited as long as the compound is made of a material capable of modifying the surface to be treated to be water-repellent. In the present embodiment, it is preferable to use a compound A or a compound A1 to be described later, and it is more preferable to use a fluorine-containing compound A-1 to be described later.

By performing chemical modification using the fluorine-containing compound A-1, it is possible to increase a contact angle of the surface to be treated to water, and to modify the surface to be treated to be water-repellent.

In Step A, after combining the first photodegradable coupling agent with the substrate, a degradable group is decomposed from an exposure unit by exposing the surface to be treated with light of a predetermined pattern, and an amino group having hydrophilic performance is generated.

As light to be applied at the time of exposure, ultraviolet rays are preferable. It is preferable that the light to be applied includes light having a wavelength of 200 nm to 450 nm and more preferable that the light to be applied includes light having a wavelength of 320 nm to 450 nm. Further, it is also preferable that the light to be applied includes light having a wavelength of 365 nm. The light having these wavelengths can efficiently degrade a photodegradable group. Examples of the light source include a low-pressure mercury lamp, a high-pressure mercury lamp, an ultrahigh-pressure mercury lamp, a xenon lamp, and a sodium lamp; a gas laser such as nitrogen, a liquid laser of an organic dye solution, and a solid-state laser obtained by allowing an inorganic single crystal to contain rare earth ions.

As a light source other than the laser from which monochromatic light is obtained, light having a specific wavelength, in which a broadband line spectrum or a continuous spectrum is extracted using an optical filter such as a band pass filter or a cutoff filter, may be used. From the viewpoint that a large area can be irradiated at once, a high-pressure mercury lamp or an ultrahigh-pressure mercury lamp is preferable as a light source.

According to the pattern formation method of the present embodiment, light can be optionally applied within the above-described range, but it is preferable that light energy showing distribution particularly corresponding to a circuit pattern is applied.

In the present step, a photodegradable group is decomposed, and an amino group is generated by irradiating the chemically modified surface to be treated with light of a predetermined pattern. The pattern is preferably a circuit pattern, and it is preferable that a circuit pattern is formed on a flexible substrate.

An example of chemical modification in the present step will be described.

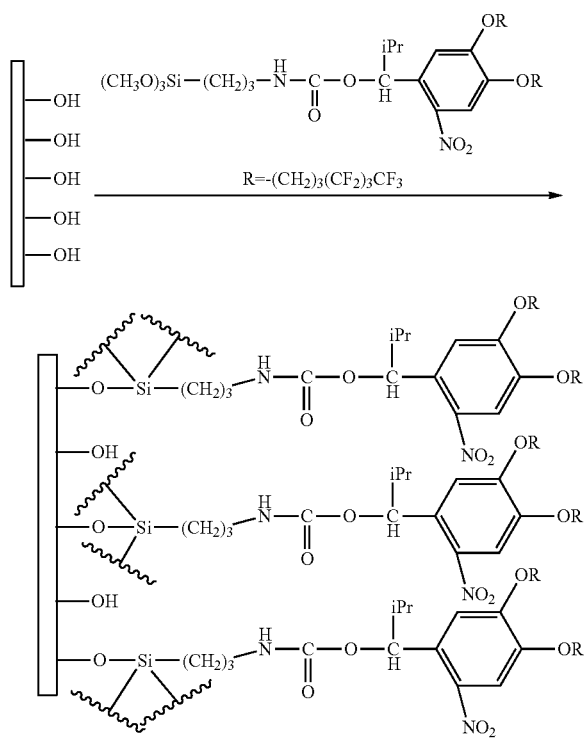

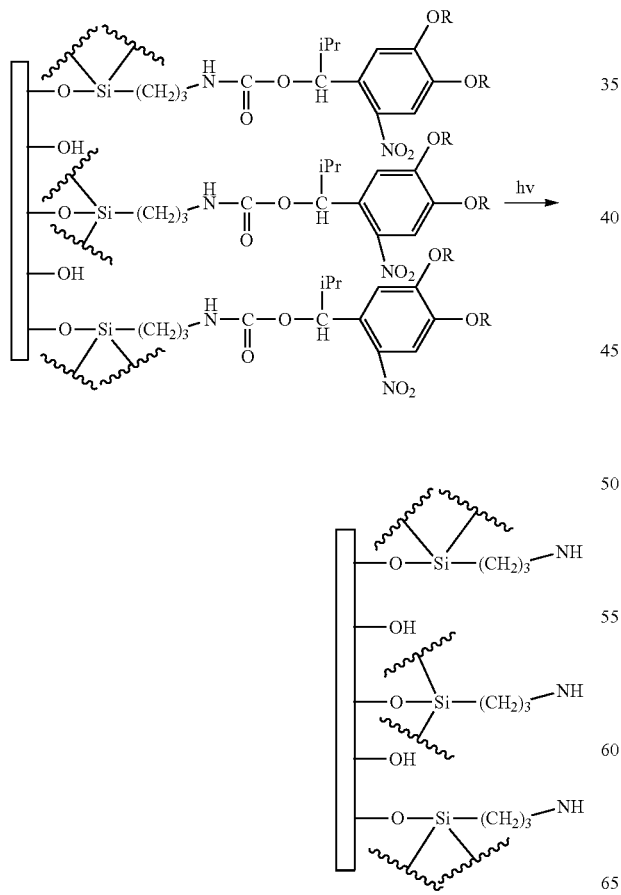

[Step B]

The present step is a step of introducing a group having semiconductor characteristics onto the surface to be treated using a first coupling agent containing a compound including the group having semiconductor characteristics, after Step A. In Step B, it is possible for a compound B to be described later to react with a remaining non-modified hydroxyl group in Step A, and to introduce the group having semiconductor characteristics onto the surface of the object. As a compound including a group having semiconductor characteristics contained in the first coupling agent, the compound B to be described later is preferably used.

An example of chemical modification in the present step will be described.

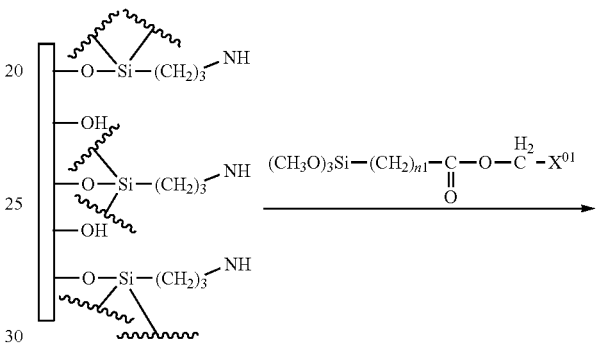

[Step C]

The present step is a step of introducing the group having semiconductor characteristics using a second coupling agent including the compound of the first embodiment of the present invention, after Step B. Descriptions related to Step C is the same as descriptions of the second step of the pattern formation method of the fourth embodiment of the present invention.

An example of chemical modification in the present step will be described.

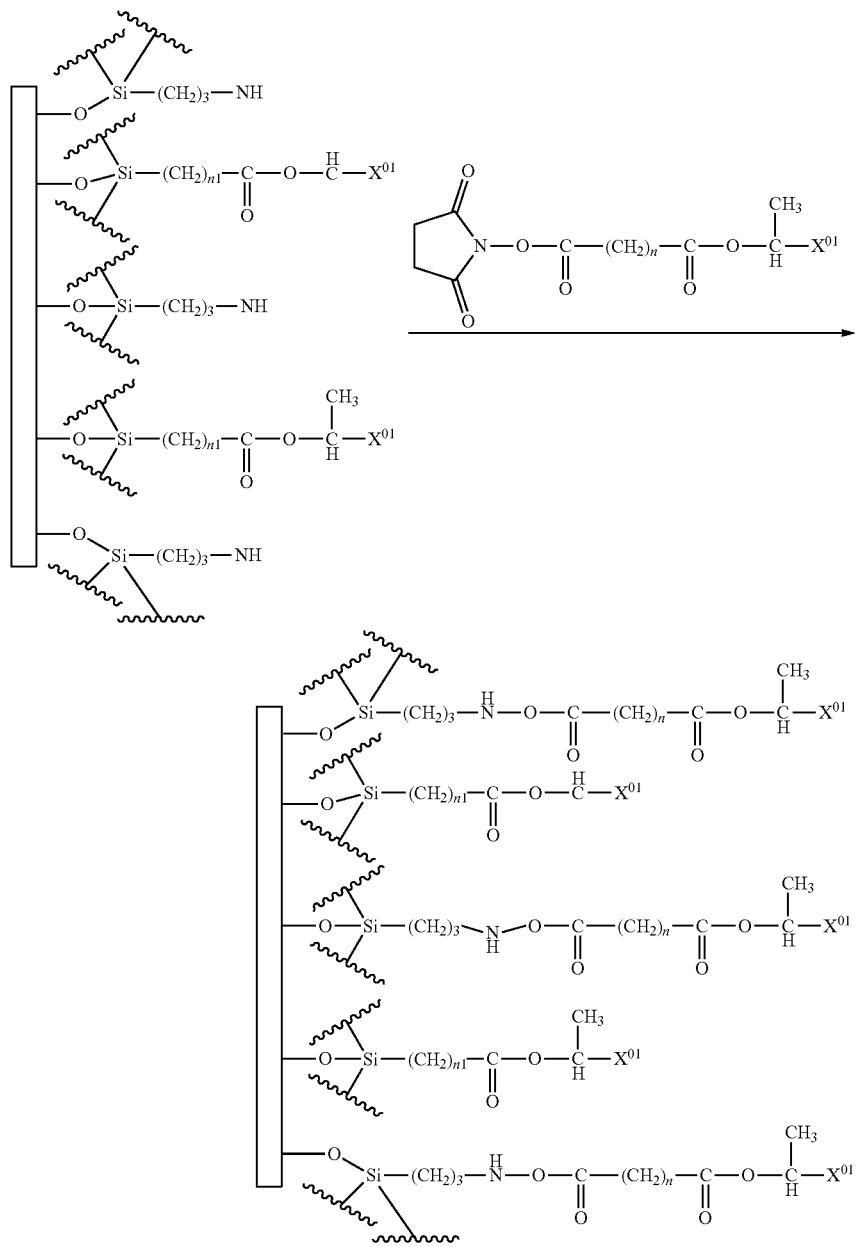

According to the present embodiment, it is possible to modify the first coupling agent including the group having semiconductor characteristics and the second coupling agent in multiple stages, and to introduce the group having semiconductor characteristics onto a surface of a substrate.

After introducing the group having semiconductor characteristics onto the surface of the substrate, an optional Step D to be described later is preferably further included. The step D is a step of further disposing a pattern forming material on the formed pattern. In Step D, it is preferable that the semiconductor characteristic group is introduced at a high density in order to further easily dispose the pattern forming material. In addition, it is preferable that surface roughness after introduction of the semiconductor characteristic group is decreased.

According to the present embodiment, the group having semiconductor characteristics is introduced in multiple stages, and thus it is possible to introduce the semiconductor characteristic group at a high density.

In addition, the second coupling agent used in Step C uses the compound of the first embodiment of the present invention. The compound of the first embodiment can decrease surface roughness after introduction of the semiconductor characteristic group by adjusting a length of an alkylene chain which is a linker structure. Specifically, when explained using the example, it is possible to align unevenness of the surface and to decrease the surface roughness by adjusting the alkylene chain so as to satisfy "$n1=3+n$".

The pattern formation method of the fourth embodiment and the pattern formation method of the fifth embodiment of the present invention preferably further include Step D. That is, the pattern formation method of the fourth embodiment preferably includes the first step, the second step, and Step D in this order, and the pattern formation method of the fifth embodiment preferably includes Step A, Step B, Step C, and Step D in this order.

[Step D]

The present step is a step of disposing a pattern forming material in a region on which a pattern is formed.

Examples of the pattern forming material include a conductive material (metal solution) obtained by dispersing particles of gold, silver, copper, alloys of these, or the like in a predetermined solvent, a precursor solution containing the above-described metals, an electronic material obtained by dissolving an insulator (resin), a semiconductor, an organic EL light emitting material, or the like in a predetermined solvent, and a resist solution. Among these, as the pattern forming material, the electronic material is preferably disposed.

According to the pattern formation method of the present embodiment, it is preferable that the pattern forming material is a conductive material, a semiconductor material, or an insulating material. Among these, a semiconductor material can be suitably disposed.

As the conductive material, a pattern forming material formed of a dispersion liquid obtained by dispersing conductive fine particles in a dispersion medium is exemplified. As the conductive fine particles, for example, metal fine particles containing any of gold, silver, copper, palladium, nickel, and ITO, oxides of these, conductive polymers, and fine particles of a superconductor are used.

These conductive fine particles can be used by coating the surface thereof with an organic substance in order to improve the dispersibility.

The dispersion medium is not particularly limited as long as the above-described conductive fine particles can be dispersed in the dispersion medium and aggregation does not occur. Examples of the dispersion medium include water; alcohols such as methanol, ethanol, propanol, and butanol; hydrocarbon-based compounds such as n-heptane, n-octane, decane, dodecane, tetradecane, toluene, xylene, cymene, durene, indene, dipentene, tetrahydronaphthalene, decahydronaphthalene, and cyclohexylbenzene; ether-based compounds such as ethylene glycol dimethyl ether, ethylene glycol diethyl ether, ethylene glycol methyl ethyl ether, diethylene glycol dimethyl ether, diethylene glycol diethyl ether, diethylene glycol methyl ethyl ether, 1,2-dimethoxyethane, bis(2-methoxyethyl)ether, and p-dioxane; and polar compounds such as propylene carbonate, γ-butyrolactone, N-methyl-2-pyrrolidone, dimethylformamide, dimethyl sulfoxide, and cyclohexanone. Among these, from the viewpoints of the dispersibility of fine particles, stability of the dispersion liquid, and ease of application to a liquid droplet discharging method (ink jet method), water, alcohols, hydrocarbon-based compounds, and ether-based compounds are preferable. As the dispersion medium, water and hydrocarbon-based compounds are more preferable.

As the semiconductor material, an organic semiconductor material formed of a dispersion liquid obtained by dispersing or dissolving the material in a dispersion medium can be used. As the organic semiconductor material, a low-molecular weight material or a polymer material of a π-electron conjugated system in which the skeleton thereof is formed of a conjugated double bond is desirable. Typical examples thereof include soluble low-molecular weight materials, for example, acenes such as pentacene, and thienoacenes such as benzothienobenzothiophene; and soluble polymer materials such as polythiophene, poly(3-alkylthiophene), and a polythiophene derivative. Further, a soluble precursor material which is changed to the above-described semiconductor through a heat treatment may be used, and examples of the pentacene precursor include sulfinylacetamide pentacene. In addition, the semiconductor material is not limited to the organic semiconductor materials, and inorganic semiconductor materials may be used.

Examples of the insulating material include insulating materials formed of a dispersion medium obtained by dispersing or dissolving polyimide, polyamide, polyester, acryl, phosphorus glass (PSG), borophosphosilicate glass (BPSG), polysilazane-based spin on glass (SOG), silicate-based SOG alkoxy silicate-based SOG, $SiO_2$ having a $Si$—$CH_3$ bond represented by a siloxane polymer, or the like in a dispersion liquid.

As the pattern forming material disposed in Step D, it is preferable to use a pattern forming material including a compound having the same or similar mother skeleton as that of the group having semiconductor characteristics introduced in Step C.

In the present step, as a method of disposing the pattern forming material, a liquid droplet discharging method, an ink jet method, a spin coat method, a roll coat method, a slot coat method, a dip coat method, or the like can be employed.

Hereinafter, each material capable of being used in the present embodiment will be described.

<<Compound A>>

A compound A relates to a compound represented by Formula (A).

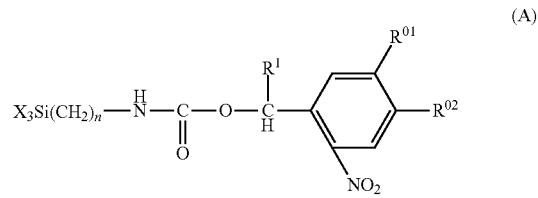

[in Formula (A), X represents a halogen atom or an alkoxy group. $R^1$ represents a hydrogen atom or a linear, branched, or cyclic alkyl group having 1 to 10 carbon atoms, $R^{01}$ and $R^{02}$ each independently represent a hydrocarbon group which may have a substituent, and n represents an integer of 0 or greater]

In Formula (A), X represents a halogen atom or an alkoxy group. Examples of the halogen atom represented by X include a fluorine atom, a chlorine atom, a bromine atom, or an iodine atom, but X is preferably an alkoxy group rather than the halogen atom. n represents an integer, and from a viewpoint of easiness of acquisition of a starting raw material, n is preferably an integer of 1 to 20 and more preferably an integer of 2 to 15.

In Formula (A), R1 represents a hydrogen atom or a linear, branched, or cyclic alkyl group having 1 to 10 carbon atoms.

As the alkyl group as $R^1$, a linear or branched alkyl group having 1 to 5 carbon atoms is preferable, and examples thereof include a methyl group, an ethyl group, a propyl group, an isopropyl group, an n-butyl group, an isobutyl group, a tert-butyl group, a pentyl group, an isopentyl group, and a neopentyl group.

Examples of the cyclic alkyl group include a group obtained by removing one or more hydrogen atoms from polycycloalkane such as monocycloalkane, bicycloalkane, tricycloalkane, and tetracycloalkane.

In the present embodiment. $R^1$ is preferably a hydrogen atom, a methyl group, an ethyl group, or an isopropyl group, but the methyl group or the isopropyl group is more preferable.

In Formula (A), $R^{o1}$ and $R^{o2}$ each independently represent a hydrocarbon group which may have a substituent.

In the present specification, in a case where "may include a substituent" is described, there included both of the case where a hydrogen atom (—H) is substituted with a monovalent group and the case where a methylene group (—$CH_2$—) is substituted with a divalent group.

Examples of the hydrocarbon groups represented by $R^{o1}$ and $R^{o2}$ include a linear or branched alkyl group.

It is preferable that the linear alkyl group has 1 to 20 carbon atoms.

In a case where the alkyl group as the hydrocarbon groups represented by $R^{o1}$ and $R^{o2}$ is a short-chain alkyl group having 1 to 5 carbon atoms, there is a case where wettability becomes favorable and washing properties are high, and thus adsorbed foreign matters can be removed.

In a case where the alkyl group as the hydrocarbon groups represented by $R^{o1}$ and $R^{o2}$ is a long-chain alkyl group having 10 or greater carbon atoms, the compound 1 can be a water-repellent compound.

In Formula (A), examples of the substituent that may be included in $R^{o1}$ and $R^{o2}$ include a substituent including an alkyl group, an alkoxy group, a halogen atom, a halogenated alkyl group, a hydroxyl group, a carbonyl group, and a hetero atom.

The alkyl group as the substituent is preferably an alkyl group having 1 to 5 carbon atoms, and most preferably a methyl group, an ethyl group, a propyl group, an n-butyl group, and a tert-butyl group.

The alkoxy group as the substituent is preferably an alkoxy group having 1 to 5 carbon atoms, preferably a methoxy group, an ethoxy group, an n-propoxy group, an iso-propoxy group, an n-butoxy group, a tert-butoxy group, and most preferably a methoxy group and an ethoxy group.

Examples of the halogen atom as the substituent include a fluorine atom, a chlorine atom, a bromine atom, and an iodine atom, and the fluorine atom is preferable.

Examples of the halogenated alkyl group as the substituent include a group obtained by substituting a part or all of the hydrogen atom of the alkyl group with the halogen atom.

As the substituent including a hetero atom, —O—, —C(=O)—O—, —S—, —S(=O)$_2$—, and —S(=O)$_2$—O— are preferable.

In Formula (A), n represents an integer of 0 or greater. In the present embodiment, n is preferably 3 or greater. In addition, n is preferably 10 or less, and more preferably 5 or less.

The upper limit and the lower limit can be optionally combined.

The compound (A) represented by Formula (A) is preferably a fluorine-containing compound (A)-1 represented by Formula (A)-1.

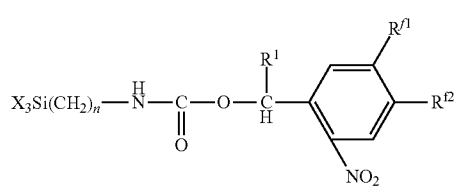

(A)-1

[in Formula (A)-1. X represents a halogen atom or an alkoxy group, $R^1$ represents a hydrogen atom or a linear, branched, or cyclic alkyl group having 1 to 10 carbon atoms, $R^{f1}$ and $R^{f2}$ each independently represent a fluorinated alkoxy group, and n represents an integer of 0 or greater]

In Formula (A)-1, description related to X, $R^1$, and n is the same as described above.

In Formula (A)-1, $R^{f1}$ and $R^{f2}$ each independently represent a fluorinated alkoxy group.

In Formula (A)-1, the fluorinated alkoxy group represented by $R^{f1}$ and $R^{f2}$ is preferably an alkoxy group having 3 or greater carbon atoms, and may be a partially fluorinated group, or may be a perfluoroalkoxy group. In the present embodiment, the fluorinated alkoxy group represented by $R^{f1}$ and $R^{f2}$ is preferably a fluorinated alkoxy group which is partially fluorinated.

In the present embodiment, examples of the fluorinated alkoxy group represented by $R^{f1}$ and $R^{f2}$ include —O—$(CH_2)_{n^{f1}}$-$(C_{n^{f2}}F_{2n^{f2}+1})$. The $n^{f1}$ is an integer of 0 or greater, and $n^{f2}$ is an integer of 0 or greater. The fluorinated alkoxy group represented by $R^{f1}$ and $R^{f2}$ may be the same or different, but from a viewpoint of easiness of synthesis, is preferably the same with each other.

In the present embodiment, the fluorinated alkoxy group represented by $R^{f1}$ and $R^{f2}$ is preferably a long-chain fluoroalkyl chain.

In the present embodiment, $n^{f1}$ is preferably 0 to 10, more preferably 0 to 5, particularly preferably 0 to 3, and extremely preferably 3.

In addition, in the present embodiment, $n^{f2}$ is preferably 1 to 15, more preferably 4 to 15, particularly preferably 6 to 12, and extremely preferably 7 to 10.

Hereinafter, specific examples of the compound represented by Formula (A) and a fluorine-containing compound represented by Formula (A)-1 will be shown.

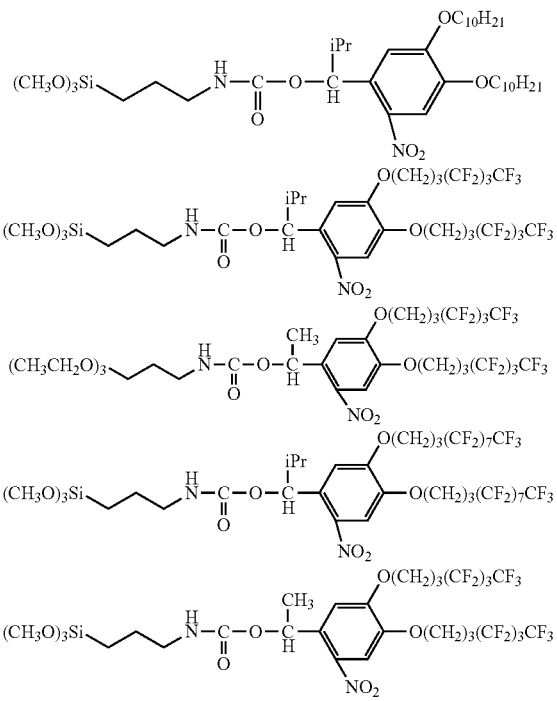

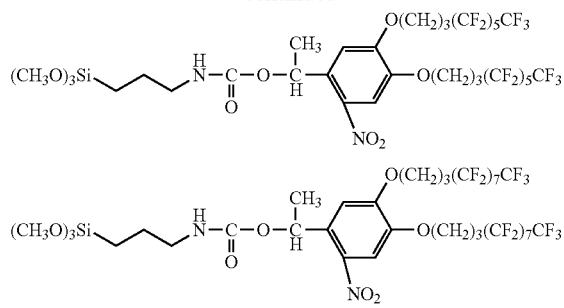

<<Compound A1>>

A compound A1 relates to a compound represented by Formula (A1).

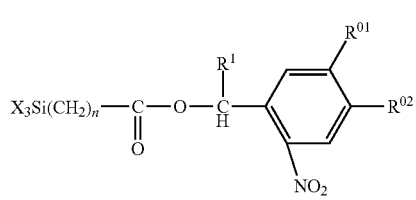

[in Formula (A1), X represents a halogen atom or an alkoxy group, $R^1$ represents a hydrogen atom or a linear, branched, or cyclic alkyl group having 1 to 10 carbon atoms, $R^{01}$ and $R^{02}$ each independently represent a hydrocarbon group which may have a substituent, and n represents an integer of 0 or greater]

In Formula (A1), description regarding X, $R^1$, $R^{01}$, $R^{02}$, and n is the same as the description regarding $R^1$, $R^{01}$, $R^{02}$, and n in Formula (A1).

The compound (A1) represented by Formula (A1) is preferably the fluorine-containing compound (A1)-1 represented by Formula (A1)-1.

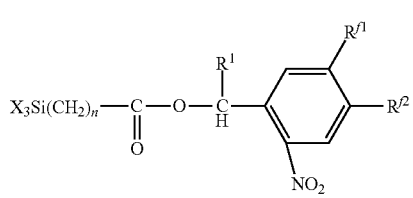

[in Formula (A1)-1, X represents a halogen atom or an alkoxy group, $R^1$ represents a hydrogen atom or a linear, branched, or cyclic alkyl group having 1 to 10 carbon atoms, $R^{f1}$ and $R^{f2}$ each independently represent a fluorinated alkoxy group, and n represents an integer of 0 or greater]

In Formula (A1)-1, description regarding X, $R^1$, $R^{f1}$, $R^{f2}$, and n is the same as the description regarding $R^1$, $R^{f1}$, $R^{f2}$, and n in Formula (A1)-1.

Hereinafter, preferable specific examples of the compound represented by Formula (A1) and the fluorine-containing compound (A1)-1 represented by Formula (A1)-1 will be shown below.

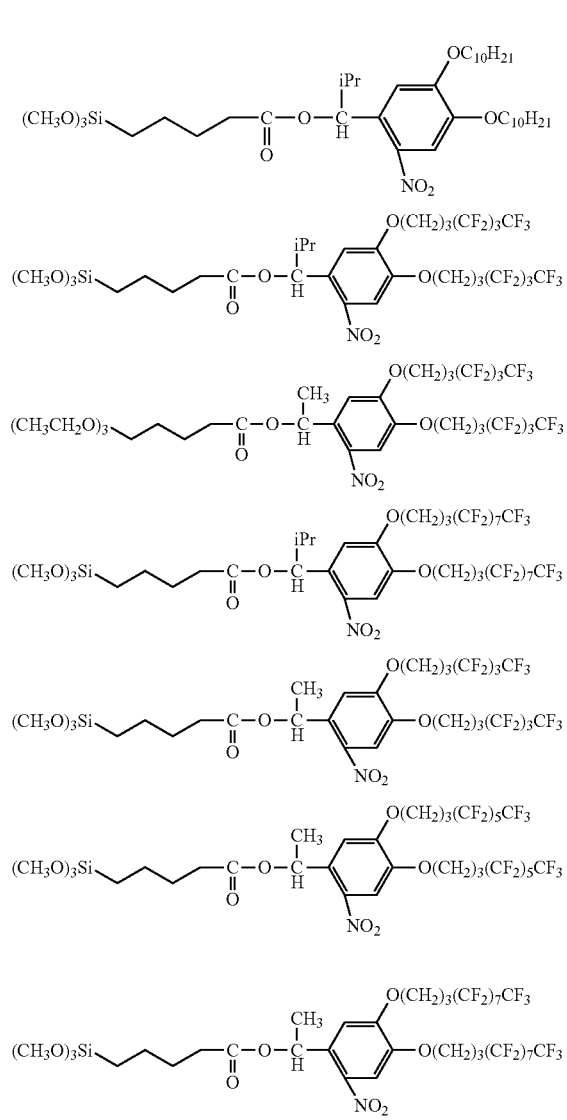

<<Compound B>>

A compound B relates to a compound represented by Formula (B).

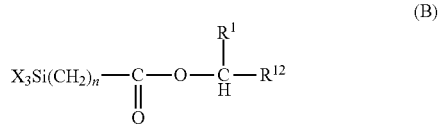

[in Formula (B), X represents a halogen atom or an alkoxy group, $R^1$ represents a hydrogen atom or a linear, branched, or cyclic alkyl group having 1 to 10 carbon atoms. $R^{12}$ represents a substituent having a thiophene skeleton, and n represents an integer of 0 or greater]

In Formula (B), description regarding X, $R^1$, and n is the same as description regarding X, $R^1$, and n in Formula (A).

Examples of a substituent having a thiophene skeleton represented by $R^{12}$ include a group represented by any one of ($R^{12}$-1) to ($R^{12}$-3).

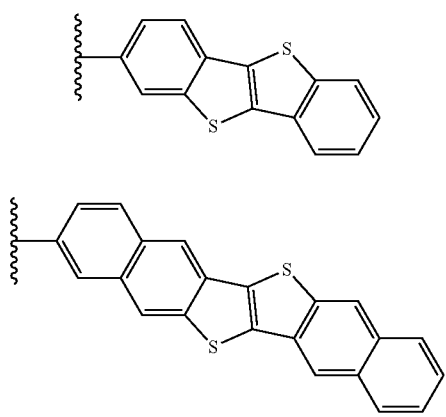 (R^{12}-1)
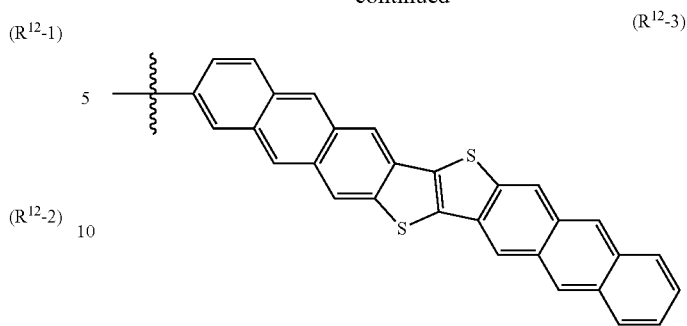 (R^{12}-3)
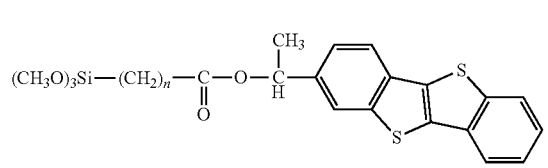 (R^{12}-2)
[in (R^{12}-1) to (R^{12}-3), the wavy line part in Formula (B) indicates a joint with a carbon atom to which R^{12} binds]
Hereinafter, specific examples of the compound represented by Formula (B) will be described below.
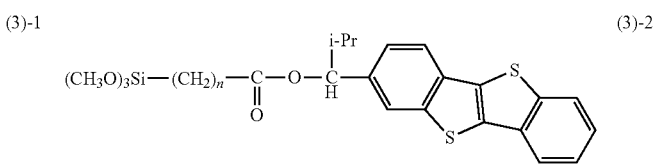 (3)-1
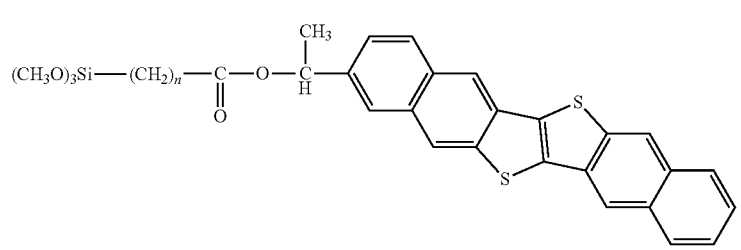 (3)-2
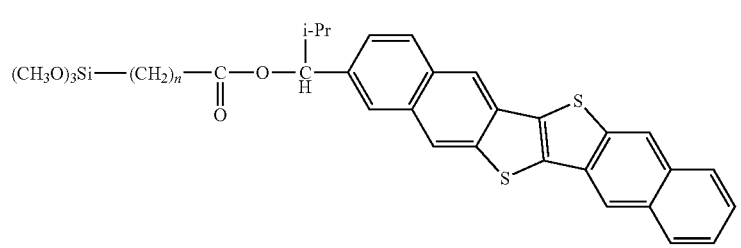 (3)-3
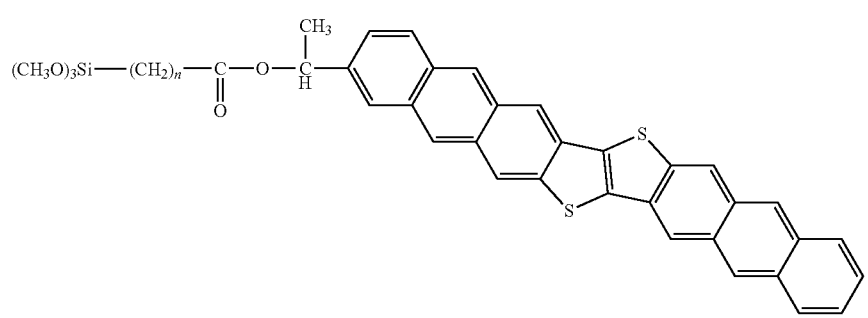 (3)-4
(3)-5

-continued (3)-6

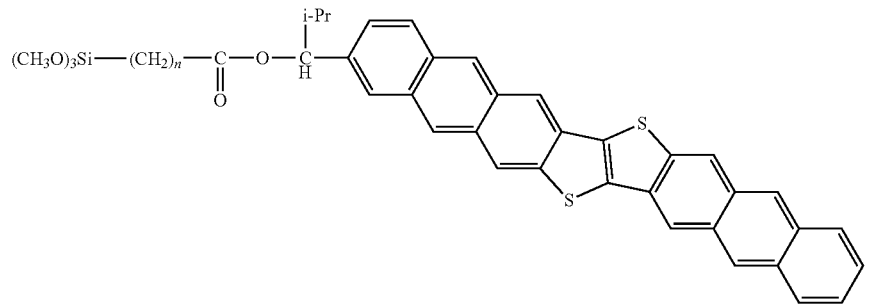

The compound B may be a compound (B1) represented by Formula (B1).

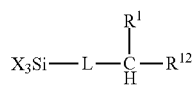

(B1)

[in Formula (B1), X represents a halogen atom or an alkoxy group, $R^1$ represents a hydrogen atom or a linear, branched, or cyclic alkyl group having 1 to 10 carbon atoms, $R^{12}$ represents a substituent having a thiophene skeleton, and L represents a divalent linking group including (—NH—) or a methylene group]

In Formula (B1), description regarding X and $R^1$ is the same as description regarding X and $R^1$ in Formula (A).

Examples of the substituent having a thiophene skeleton represented by $R^{12}$ include a group represented by any one of ($R^{12}$-1) to ($R^{12}$-3).

The compound (B1) can be obtained by reacting a silane compound with the compound represented by Formula (1) and changing an active carbonate structure.

As described above, the compound represented by Formula (1) can simultaneously perform modification of an aminated substrate and introduction of a semiconductor characteristic group. The compound represented by Formula (1) can be a material into which a group having semiconductor characteristics is introduced onto a surface of an object having a hydroxyl group by changing a part of the structure.

In addition, the compound (B1) is preferably a compound (B1)-1 represented by Formula (B1)-1.

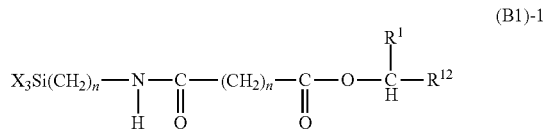

(B1)-1

[in Formula (B1)-1, X represents a halogen atom or an alkoxy group, $R^1$ represents a hydrogen atom or a linear, branched, or cyclic alkyl group having 1 to 10 carbon atoms, $R^{12}$ represents a substituent having a thiophene skeleton, and n represents an integer of 0 or greater]

In Formula (B1)-1, description regarding X, $R^1$, and n is the same as description regarding X, $R^1$, and n in Formula (A).

Examples of the substituent having a thiophene skeleton represented by $R^{12}$ include a group represented by any one of ($R^{12}$-1) to ($R^{12}$-3).

Preferable specific examples of the compound (B1) will be described below. In the specific examples of the compound (B1), n represents any one integer of 1 to 20, but is preferably 1 to 15, more preferably 5 to 10, and particularly preferably 7 or 10.

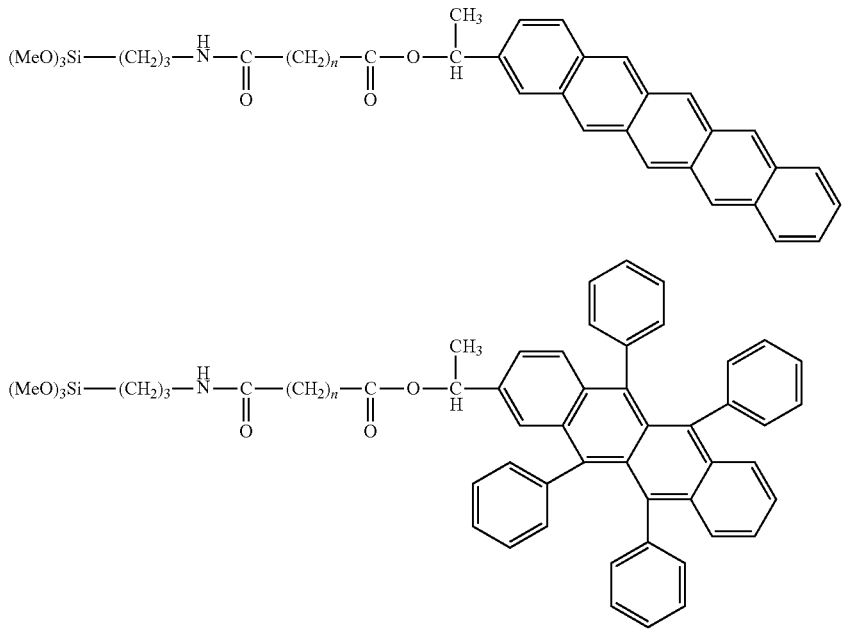

-continued

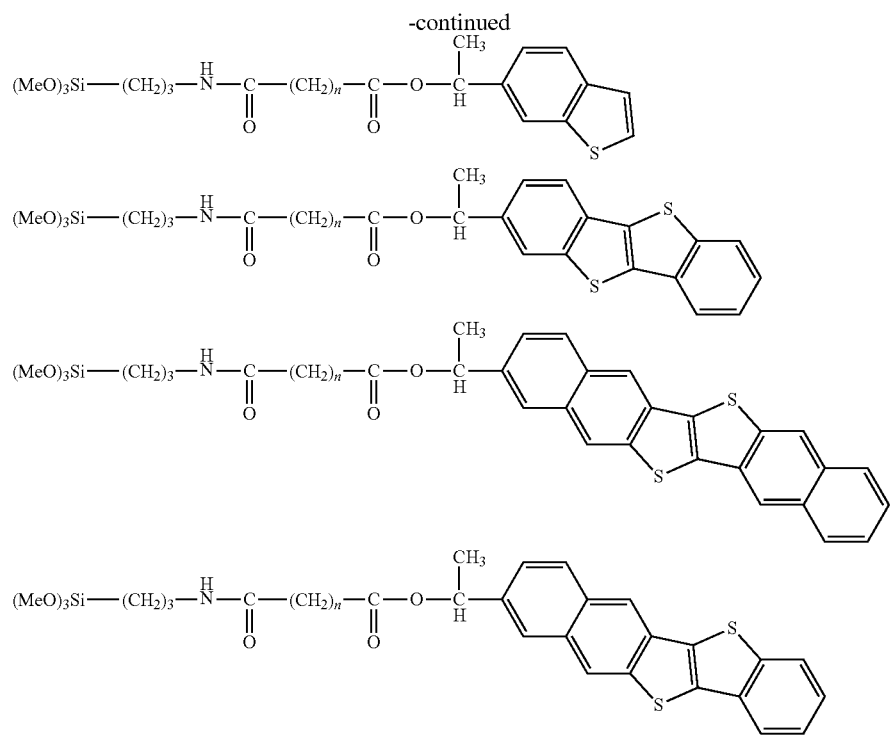

Hereinafter, the pattern formation method according to the present embodiment will be described with reference to the accompanying drawings.

According to the pattern formation method of the present embodiment, in a case where a flexible substrate compatible with a so-called roll-to-roll process is used, a pattern may be formed using a substrate treatment device 100 which is a roll-to-roll device as shown in FIG. 1. The configuration of the substrate treatment device 100 is shown in FIG. 1.

As shown in FIG. 1, the substrate treatment device 100 includes a substrate supply unit 2 which supplies a stripe-shaped substrate (for example, a stripe-shaped film member) S; a substrate treatment unit 3 which performs a treatment on a surface (surface to be treated) Sa of the substrate S; a substrate recovery unit 4 which recovers the substrate S; a coating unit 6 which applies the compound according to the first embodiment; an exposure unit 7; a mask 8; a patterned material coating unit 9; and a control unit CONT which controls each unit. The substrate treatment unit 3 can perform various treatments on the surface of the substrate S between the time at which the substrate S is sent out from the substrate supply unit 2 and the time at which the substrate S is recovered by the substrate recovery unit 4.

The substrate treatment device 100 can be suitably used in a case where a display element (electronic device) such as an organic EL element or a liquid crystal display element is formed on the substrate S.

Further, FIG. 1 shows a system of using a photomask for generating light having a desired pattern, but the present embodiment can also be suitably applied to a maskless exposure system that does not use a photomask. Examples of the maskless exposure system of generating patterned light without using a photomask include a method of using a spatial light modulation element such as DMD, and a system of scanning spot light such as a laser beam printer.

Hereinafter, the pattern formation method according to the present embodiment will be described appropriately using an XYZ coordinate system after the XYZ coordinate system is set as shown in FIG. 1. In the XYZ coordinate system, for example, an X axis and a Y axis are set along the horizontal plane, and a Z axis is set upward along the vertical direction. Further, the overall substrate treatment device 100 is along the X axis, and the substrate S is transported from a negative side (−side) to a positive side (+side). At this time, the width direction (short length direction) of the stripe-shaped substrate S is set as the Y axis direction.

As the substrate S to be treated in the substrate treatment device 100, for example, a resin film or foil such as stainless steel can be used. Examples of the resin film include materials such as a polyethylene resin, a polypropylene resin, a polyester resin, an ethylene vinyl copolymer resin, a polyvinyl chloride resin, a cellulose resin, a polyamide resin, a polyimide resin, a polycarbonate resin, a polystyrene resin, and a vinyl acetate resin.

It is preferable that the thermal expansion coefficient of the substrate S is small so that the size thereof is not changed even in a case of being heated at approximately 200° C. The thermal expansion coefficient can be decreased by mixing an inorganic filler into the resin film. Examples of the inorganic filler include titanium oxide, zinc oxide, alumina, and silicon oxide. Further, the substrate S may be a single ultrathin glass having a thickness of approximately 100 μm which has been produced by a float glass method or the like or a laminate obtained by bonding the resin film or an aluminum foil to this ultrathin glass.

The substrate S is formed such that the size thereof in the width direction (short length direction) is in a range of 1 m to 2 m and the size thereof in the length direction (long length direction) is 10 m or longer. These sizes are merely an example and are not limited thereto. For example, the size of the substrate S in the Y direction may be 50 cm or shorter or 2 m or longer. Further, the size of the substrate S in the X direction may be 10 m or shorter.

It is preferable that the substrate S is formed to have a flexibility. Here, the flexibility indicates a property in which the substrate can be bent without being cut or fractured even in a case where a force with a degree of the own weight of the substrate is applied to the substrate. Further, the concept of the flexibility also includes a property in which the substrate is bent by a force with a degree of the own weight of the substrate.

Further, the flexibility varies depending on the material of the substrate, the size, the thickness, or the environment such as the temperature. In addition, as the substrate S, a single strip-shaped substrate may be used or a substrate having a configuration in which a plurality of unit substrates are connected to be formed into a strip shape may be used.

The substrate supply unit 2 sends out and supplies the substrate S wound in a roll shape to the substrate treatment unit 3. In this case, a shaft that winds the substrate S, a rotary driving device that rotates the shaft, and the like are provided in the substrate supply unit 2. In addition, a configuration in which a cover portion or the like that covers the substrate S in a state of being wound in a roll shape is provided may be employed. Further, the substrate supply unit 2 is not limited to the mechanism of sending out the substrate S wound in a roll shape and may have a mechanism (for example, a nip type driving roller) of sequentially sending out the stripe-shaped substrate S in the length direction thereof.

The substrate recovery unit 4 recovers the substrate S having passed through the substrate treatment device 100 by means of winding the substrate S, for example, in a roll shape. Similar to the substrate supply unit 2, the substrate recovery unit 4 is provided with a shaft for winding the substrate S, a rotary driving source that rotates the shaft, a cover portion that covers the recovered substrate S, and the like. Further, in a case where the substrate S in the substrate treatment unit 3 is cut into a panel shape, for example, the substrate is recovered in a state of being overlapped. In other words, a configuration in which the substrate S is recovered in a state different from the state in which the substrate S is wound in a roll shape may be employed.

The substrate treatment unit 3 performs a step of transporting the substrate S supplied from the substrate supply unit 2 to the substrate recovery unit 4 and chemically modifying the surface Sa to be treated of the substrate S using the compound according to the first embodiment during the process of transportation; a step of irradiating the chemically modified surface to be treated with light in a predetermined pattern; and a step of disposing the pattern forming material. The substrate treatment unit 3 includes a compound coating unit 6 which coats the surface Sa to be treated of the substrate S with the compound according to the first embodiment; an exposure unit 7 which irradiates the surface with light; a mask 8; a patterned material coating unit 9; and a transport device 20 which includes a driving roller R and the like for sending the substrate S under conditions compatible with the form of the processing treatment.

As the compound coating unit 6 and the patterned material coating unit 9, liquid droplet coating devices (such as a liquid droplet discharge type coating device, an ink jet type coating device, a spin coat type coating device, a roll coat type coating device, and a slot coat type coating device) are exemplary examples.

Each of these devices is appropriately provided along the transport path of the substrate S, and a panel and the like of a flexible display can be produced using a so-called roll-to-roll system. In the present embodiment, the exposure unit 7 is provided and a device that performs steps (a photosensitive layer formation step, a photosensitive layer development step, and the like) before and after the steps described above is also provided inline as necessary.

EXAMPLES

Hereinafter, the present invention will be described in more detail based on the examples, but the present invention is not limited to the following examples.

Synthesis Example 1 of Compound

Synthesis of benzothieno[3,2-b][1]benzothiophene (BTBT)

10.0 g (71.1 mmol) of o-chlorobenzaldehyde, 7.98 g (142 mmol) of sodium hydrogen sulfide hydrate, and 100 mL of N-methyl pyrrolidone (NMP) were added to a 300-mL eggplant flask, and the solution was stirred for 1 hour at 80° C. and for 1 hour at 180° C. After that, the reaction solution was cooled to near room temperature, and poured into 100 mL of a saturated ammonium chloride aqueous solution. The resultant product was cooled in an ice bath, and a generated brown precipitate was filtered under suction. The residue was washed with water and acetone to obtain a pale yellow solid. The solid was dissolved in chloroform, purified by column chromatography (chloroform), and concentrated. The obtained yellow solid was purified by recrystallization (120 mL of toluene, 60° C.), filtered under suction, and vacuum-dried to obtain a pale yellow solid.

Yield amount/yield rate: 1.32 g (5.48 mmol, 15%)

$R_f$: 0.83 (hexane:ethyl acetate=1:1)

$^1$H-NMR (CDCl$_3$/TMS, 400 MHz): δ=7.39 (ddd, J=7.6 Hz, 7.6 Hz, 1.2 Hz, 2H), 7.44 (ddd, J=7.6 Hz, 7.6 Hz, 1.2 Hz, 2H), 7.87 (dd, J=7.2 Hz, 0.8 Hz, 2H), 7.90 (dd, J=7.6 Hz, 0.8 Hz, 2H)

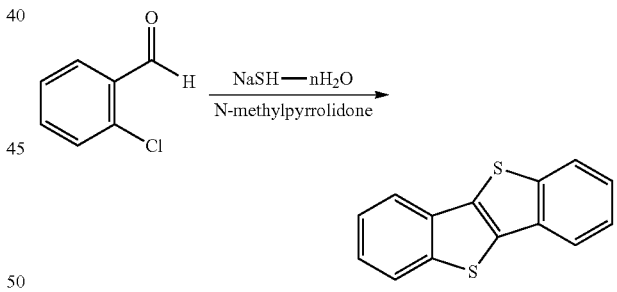

Synthesis of [1]benzothieno[3,2-b][1]benzothien-2-yl)ethane-1-one 2.01 g (8.36 mmol) of [1]benzothieno[3,2-b][1]benzothiophene (BTBT) was added to a 300 mL eggplant flask, and dissolved in 200 mL of dichloromethane. After the solution was cooled to −20° C. (ice, ethanol, liquid nitrogen), 4.27 g (32.0 mmol) of aluminum chloride was added thereto, 2.62 g (33.4 mmol) of acetyl chloride was slowly added dropwise thereto, and the solution was stirred for 1 hour. After that, the reaction solution was poured into 100 mL of water, and 100 mL of dichloromethane was added thereto. The water layer was separated from the organic layer, and the organic layer was washed with water (50 mL×6) and a brine (100 mL). The organic layer was dried with an anhydrous magnesium sulfate, filtered, and concentrated. The resultant product was isolated and purified by recrystallization (300 mL of toluene, 70° C.) and vacuum-dried to obtain a pale yellow solid.

Yield amount/yield rate: 1.93 g (6.85 mmol, 82%)

$R_f$: 0.63 (chloroform)

$^1$H-NMR (CDCl$_3$/TMS, 400 MHz): δ=2.72 (s, 3H), 7.44 to 7.52 (m, 2H), 7.93 to 7.96 (m, 3H), 8.05 to 8.08 (m, 1H), 8.56 (m, 1H)

IR (KBr): 1674 cm$^{-1}$

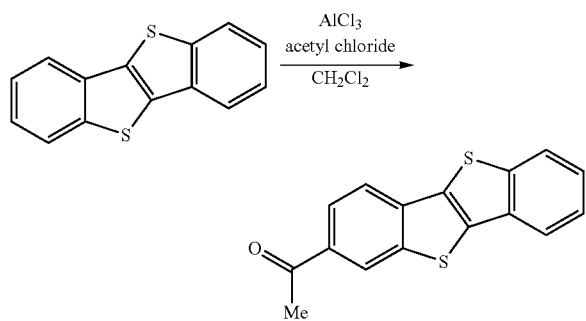

Synthesis of [1]benzothieno[3,2-b][1]benzothien-2-yl)ethane-1-ol 0.111 g (0.393 mmol) of [1]benzothieno[3,2-b][1]benzothiene-2-yl)ethane-1-one, 30 mL of tetrahydrofuran (THF), and 15 mL of methanol were put into a 100 mL eggplant flask, and 0.0297 g (0.786 mmol: 2 eq) of sodium tetraborohydride was gradually added thereto in an ice bath, and the solution was stirred for 30 minutes. After that, the solution was stirred at room temperature for 30 minutes. The reaction solution was concentrated, dissolved in 60 mL of chloroform, 20 mL of water and 5 mL of 2N hydrochloric acid were added thereto, and the water layer was separated from the organic layer. In addition, the organic layer was extracted with chloroform (20 mL×2), and dried with an anhydrous magnesium sulfate, filtered, concentrated, and vacuum-dried to obtain a white solid.

Yield amount/yield rate: 0.111 g (0.390 mmol, 99%)

$R_f$: 0.33 (chloroform)

$^1$H-NMR (CDCl$_3$/TMS, 400 MHz): δ=1.60 (d, 3H, J=6.5), 1.90 (d, 1H, J=3.2), 5.06 to 5.11 (m, 1H), 7.26 to 7.49 (m, 3H), 7.86 to 7.96 (m, 4H)

IR (KBr): 3347 cm$^{-1}$

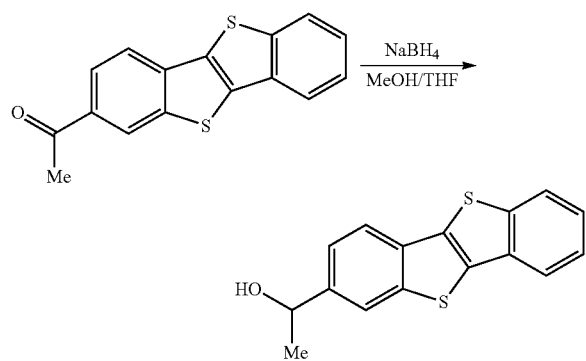

Synthesis of 9-(1-(benzo[b]benzo[4,5]thieno[2,3-d]thiophen-2-yl)ethoxy)-9-oxononanoic acid Under a nitrogen atmosphere, 0.543 g (2.83 mmol, 1.5 eq) of 1-(3-dimethyl aminopropyl)-3-ethylcarbodiimide hydrochloride (EDC/HCl), 50 mL of dry THF, and 0.768 g (4.24 mmol, 2.0 eq) of azelaic acid were added to a 200 mL two-necked eggplant flask, and the solution was stirred in an ice bath for 10 minutes. 0.523 g (1.84 mmol, 1.0 eq) of [1]benzothieno[3,2-b][1]benzothiene-2-yl)ethane-1-ol and 0.352 g (2.89 mmol, 1.5 eq) of N,N-dimethyl-4-aminopyridine (DMAP) were dissolved in 50 mL of dry-THF, and slowly added dropwise to the solution. After the dropwise addition, the ice bath was taken out, and the solution was stirred at room temperature for 16 hours. The reaction solution was concentrated and dissolved in 200 mL of ethyl acetate, 100 mL of water and 2N hydrochloric acid were added thereto to make the water layer to have acidity, and the water layer was separated from the organic layer. In addition, the organic layer was extracted with ethyl acetate (100 mL×2), and washed with a saturated ammonium chloride aqueous solution (100 mL×2). The organic layer was dried with an anhydrous magnesium sulfate, filtered, and concentrated. The resultant product was purified by column chromatography (ethyl acetate:hexane=2:1, Φ=4.3 cm, h=15 cm), concentrated, and vacuum-dried to obtain a white solid.

Yield amount: 0.271 g (0.596 mmol)

Yield rate: 32%

$^1$H-NMR (CDCl$_3$/TMS, 400 MHz): δ=1.25 to 1.31 (6H, m), 1.62 to 1.63 (9H, m), 2.32 to 2.37 (4H, m), 6.01 to 6.06 (1H, q, J=6.4 Hz), 7.39 to 7.49 and 7.85 to 7.93 (4H, m)

IR (KBr): 1692 cm$^{-1}$, 1730 cm$^{-1}$, 2919 cm$^{-1}$

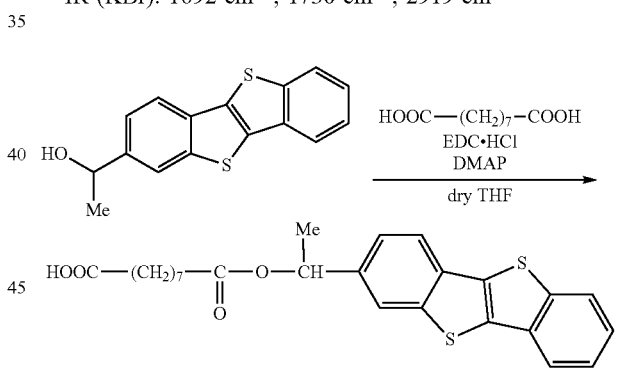

Synthesis of 1-(1-(benzo[b]benzo[4,5]thieno[2,3-d]thiophen-2-yl)ethyl)9-(2,5-dioxopyrrolidin-1-yl)nonanedioate Under a nitrogen atmosphere, 0.126 g (0.28 mmol, 1.0 eq) of 9-(1-(benzo[b]benzo[4.5]thieno[2,3-d]thiophene-2-yl)ethoxy)-9-oxononanoic acid was put in a 100 mL two-necked eggplant flask and dissolved in 75 mL of dry acetone, and 0.085 g (0.84 mmol, 3.0 eq.) of triethylamine and 0.215 g (0.84 mmol, 3.0 eq) of di(N-succinimidyl) carbonate were added thereto. After that, the solution was stirred at room temperature for 1 hour. The reaction solution was concentrated, isolated and purified by column chromatography (chloroform, Φ=3.0 cm, h=15 cm), concentrated, and vacuum-dried to obtain a white solid (compound represented by Formula (1)-1-1 of the present embodiment).

<Yield amount>0.123 g (0.224 mmol)
<Yield rate>80% (Rf=0.66, hexane:ethyl acetate=2:1)
$^1$H-NMR (CDCl$_3$/TMS, 400 MHz): δ=1.25 to 1.43 (m, 13H), 1.63 to 1.73 (m, 7H), 2.33 to 2.38 (t, 2H, J=8.0 Hz), 2.55 to 2.59 (t, 2H, J=7.6 Hz), 2.82 to 2.84 (m, 4H), 6.01 to 6.06 (q, 1H, J=6.4 Hz), 7.41 to 7.47 (m, 3H), 7.87 to 7.93 (m, 4H)

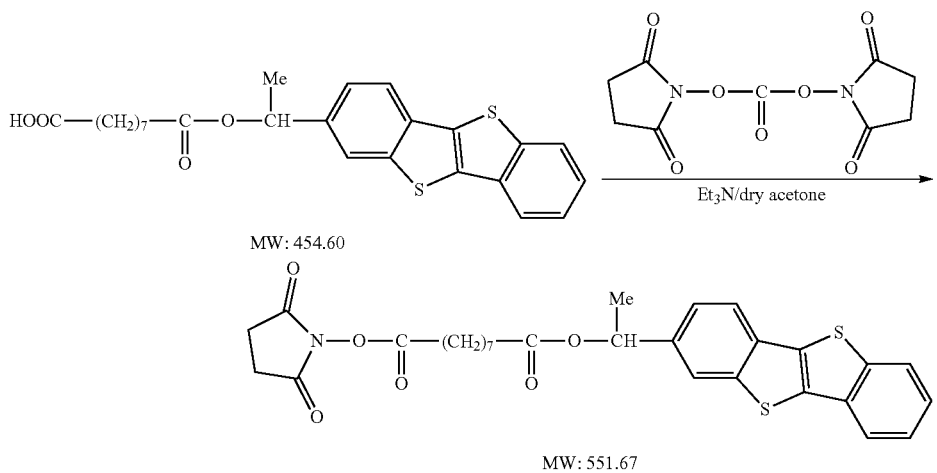

Synthesis of 1-(benzo[b]benzo[4,5]thieno[2,3-d]thiophen-2-yl)ethyl 3,3-dimethoxy-9-oxo-2,8-dioxa-7-aza-3-silaheptadecan-17-oate 150 mg (0.272 mmol, 1.0 eq.) of a raw material, 3 mL of dry-THF, 51.5 mL (0.412 mmol, 1.5 eq.) of (3-aminopropyl)trimethoxy silane, and 150 mL (0.677 mmol, 2.5 eq.) of triethylamine were added to a 20 mL two-necked eggplant flask, and the solution was stirred at room temperature for 16 hours under a nitrogen atmosphere. After that, concentration was performed, and column chromatography (hexane:ethyl acetate:tetramethyl orthosilicate=1:1:0.02, f=2.0 cm, h=8 cm), concentration, and vacuum drying (40° C.) were performed to obtain a white solid.

<Result>
Yield amount: 126 mg (0.205 mmol)
Yield amount: 75%
Rf Value: 0.50 (1:1=ethyl acetate:hexane)
$^1$H-NMR (CDCl$_3$/TMS, 400 MHz): δ=0.54 to 0.58 (2H, t, J=8.0 Hz), 1.21 (7H, m), 1.53 to 1.56 (12H, m), 2.00 to 2.05 (2H, t, J=8.0 Hz), 2.26 to 2.30 (2H, t, J=6.0 Hz), 3.13 to 3.18 (2H, q, J=6.3 Hz), 3.48 to 3.58 (10H, m), 5.53 (1H, br), 5.94 to 6.00 (1H, q, J=1.5 Hz), 7.19 to 7.42 (3H, m), 7.78 to 7.87 (4H, m)

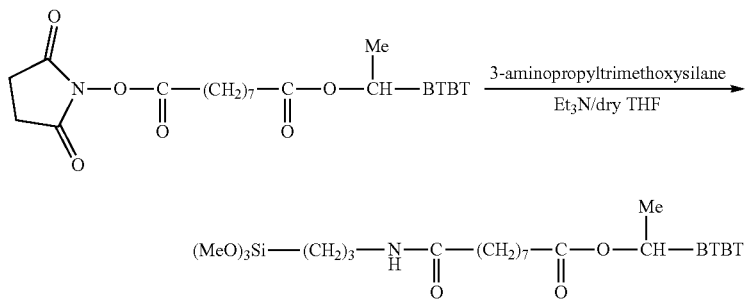

[in the formula, "BTBT" represents a group represented in the $(R^{12}\text{-}1)$]

Synthesis Example 2 of Compound

Synthesis of 12-(1-(benzo[b]benzo[4,5]thieno[2,3-d]thiophen-2-yl)ethoxy)-12-oxododecanoic acid Under a nitrogen atmosphere, 0.051 g (0.26 mmol: 1.5 eq) of EDC/HCl, 10 mL of dry THF, and 0.41 g (1.8 mmol: 10 eq) of dodecanedioic acid were added to a 100-mL two-necked eggplant flask, and the solution was stirred in an ice bath for 10 minutes, 0.050 g (0.18 mmol: 1 eq) of [1]benzothieno[3,2-b][1]benzothiene-2-yl)ethane-1-ol and 0.032 g (0.26 mmol: 1.5 eq) of DMAP were dissolved in 10 mL of dry-THF, and slowly added to the solution. After the drop-wise addition, the ice bath was taken out, and the solution was stirred at room temperature for 16 hours.

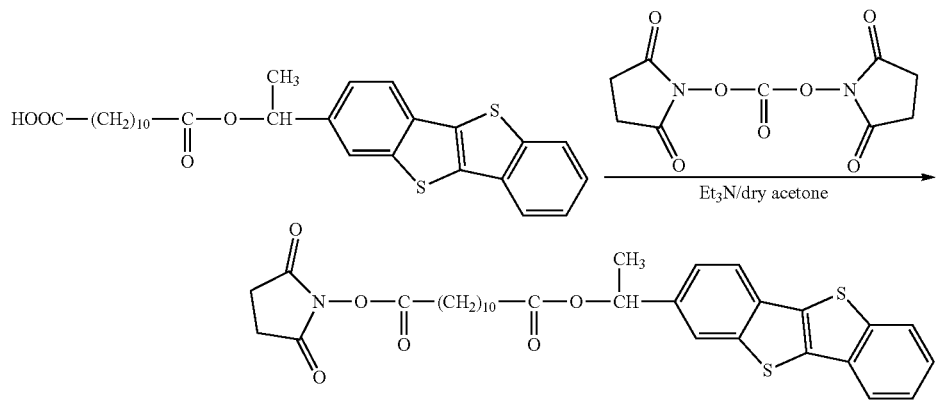

The reaction solution was concentrated and dissolved in 30 mL of ethyl acetate, 30 mL of $H_2O$ and 5 mL of 2N hydrochloric acid were added thereto, and the water layer was separated from the organic layer. In addition, the organic layer was extracted with ethyl acetate (30 mL×2), and washed with a saturated brine (30 mL×2). The organic layer was dried with an anhydrous magnesium sulfate, filtered, and concentrated. Ethanol overheated at 50° C. was added thereto, and the organic layer was filtered under suction to recover the residue. The resultant product was vacuum-dried to obtain a white solid.

Yield amount/yield rate: 0.046 g (0.093 mmol, 35%)

$R_f$: 0.30 (hexane:ethyl acetate=2:1)

$^1$H-NMR (acetone-d6/TMS, 400 MHz): δ=1.26 to 1.29 (m, 12H), 1.53 to 1.63 (m, 7H), 2.24 (t, 2H, J=7.4), 2.38 (t, 2H, J=7.4), 6.05 (q, 1H, J=6.5), 7.48 to 7.59 (m, 3H), 7.98 to 8.13 (m, 4H)

IR (KBr): 1698 cm$^{-1}$, 1731 cm$^{-1}$, 2919 cm$^{-1}$

Synthesis of 1-(1-(benzo[b]benzo [4,5]thieno[2,3-d]thiophen-2-yl)ethyl) N-succinimidyl decandioate Under a nitrogen atmosphere, 0.034 g (0.069 mmol: 1 eq) of 12-(1-(benzo[b]benzo[4,5]thieno[2,3-d]thiophene-2-yl) ethoxy)-12-oxododecanoic acid was put in a 50 mL two-necked eggplant flask and dissolved in 15 mL of dry-acetone, and 0.021 g (0.21 mmol: 3 eq) of triethylamine and 0.053 g (0.21 mmol: 3 eq) of di(N-succinimidyl) carbonate were added thereto.

After that, the solution was stirred at room temperature for 1 hour. The reaction solution was concentrated, isolated and purified by column chromatography (hexane:ethyl acetate=2:1), concentrated, and vacuum-dried to obtain a white solid (compound represented by Formula (1)-1-1 of the present embodiment).

Yield amount/yield rate: 0.040 g (0.067 mmol, 98%)

$R_f$: 0.53 (hexane:ethyl acetate=2:1)

$^1$H-NMR (CDCl$_3$/TMS. 400 MHz): δ=1.24 to 1.35 (m, 12H), 1.62 to 1.74 (m, 7H), 2.35 (t, 2H. J=7.6), 2.56 (t, 2H, J=7.6), 2.82 (s, 4H), 6.04 (q, 1H, J=6.5), 7.39 to 7.49 (m, 3H), 7.85 to 7.93 (m, 4H)

IR (KBr): 1724, 1742, 1784, 1814 cm$^{-1}$

Element analysis calculation value C, 64.73; H, 5.94: N, 2.36

Actual measurement value C, 64.72; H, 5.81; N, 2.36

REFERENCE SIGNS LIST

S: substrate
CONT: control unit
Sa: surface to be treated
2: substrate supply unit
3: substrate treatment unit
4: substrate recovery unit
6: compound coating unit
7: exposure unit
8: mask
9: patterned material coating unit
100: substrate treatment device

The invention claimed is:
1. A compound represented by Formula (1),

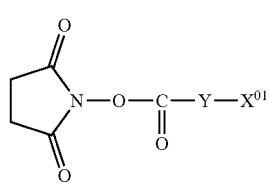

[in the formula, $X^{01}$ represents a group exhibiting semi-conductor characteristics and Y represents a divalent linking group], wherein the $X^{01}$ represents a group having a thiophene skeleton.

2. A pattern forming substrate, which has a surface chemically modified by the compound according to claim 1.

3. A coupling agent which is formed of the compound according to claim 1.

* * * * *